Figure 1:
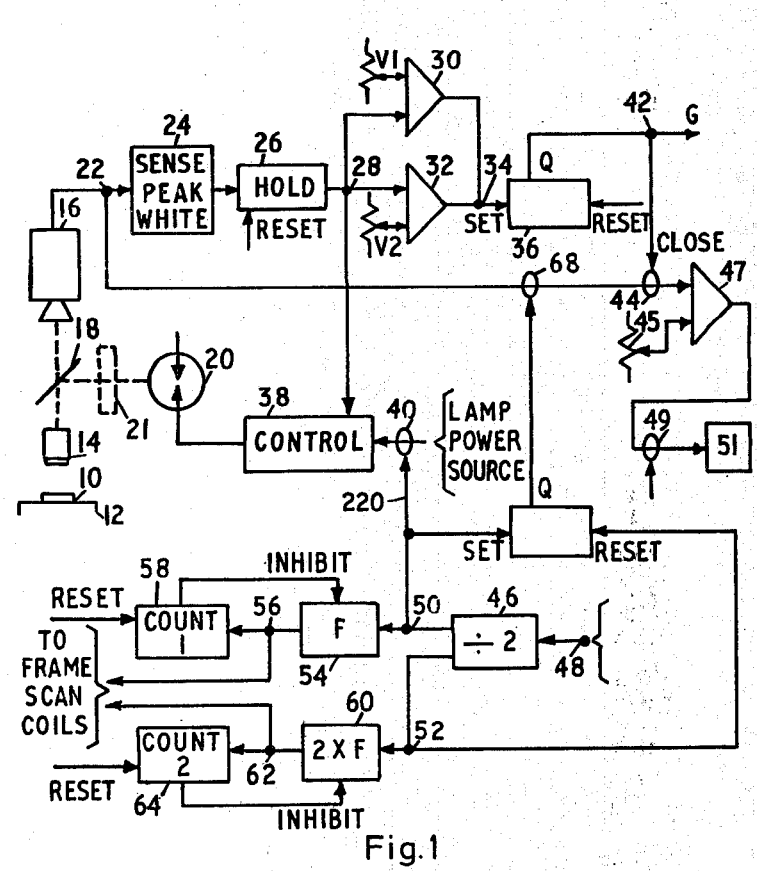

United States Patent [19]
Crawley

[11] 3,980,814
[45] Sept. 14, 1976

[54] MULTIPLE IMAGE SCANNING

[75] Inventor: John Alfred Crawley, Great Chishill, near Royston, England

[73] Assignee: Image Analysing Computers Limited, Royston, England

[22] Filed: Nov. 21, 1973

[21] Appl. No.: 417,726

[30] Foreign Application Priority Data
Nov. 21, 1972 United Kingdom............... 53743/72

[52] U.S. Cl........................... 178/7.2; 178/DIG. 36; 178/6.8
[51] Int. Cl.²........................................... H04N 3/16
[58] Field of Search........... 178/7.2, DIG. 1, DIG. 5, 178/DIG. 29, 7.6, DIG. 42, 6.8; 350/90, 91, 86; 250/311

[56] References Cited
UNITED STATES PATENTS

| | | | |
|---|---|---|---|
| 3,628,014 | 12/1971 | Grubic, Jr.................... | 178/DIG. 1 |
| 3,674,924 | 7/1972 | Fischer, et al................ | 178/DIG. 1 |
| 3,683,108 | 8/1972 | Pieters........................ | 178/DIG. 42 |
| 3,816,651 | 6/1974 | Gardner....................... | 178/7.2 |

*Primary Examiner*—John C. Martin
*Attorney, Agent, or Firm*—Oblon, Fisher, Spivak, McClelland & Maier

[57] ABSTRACT

An improvement in methods of image analysis is described whereby the time required for analyzing certain types of images can be substantially reduced. The invention utilizes the light integration characteristic of a television camera to combine a succession of images applied thereto into a single composite image. A video signal of the composite image is then obtained by scanning in the usual way. Analysis of the video signal is performed in a known manner after threshold detection.

The invention is of application to the analysis of microscopic specimens which are generally black or dark grey and which include a few widely spaced white or light grey features, on which the analysis is to be performed.

One embodiment utilizes a single scanner and switching devices for alternately producing scanning and not scanning. A second embodiment utilizes two or more scanners with switching devices for causing first one scanner and then the other to scan for reading and erasing whilst the other is quiescent and an optical diverting device for applying the images to the quiescent of the two scanners.

4 Claims, 6 Drawing Figures

MULTIPLE IMAGE SCANNING

The invention concerns image analysis systems and in particular an improvement in the mode of operation of such systems to facilitate the analysis of field which can be represented as a generally dark background containing a few widely separated, small bright features.

An image analysis system comprises a means for scanning an image to obtain a video signal and signal processing means supplied with the video signal for separating video signal content relating to selected grey level regions of the image from the remainder thereof. Typically the amplitude of the video signal varies with grey level and selection can be achieved by threshold detection in which the instantaneous amplitude excursion of the video signal is compared with a reference voltage and a two-value so-called detected signal is generated having one value when the amplitude of the video signal exceeds the threshold and its other value when the video signal amplitude is below the threshold. Measurements can be performed on the detected signal pulses thereby allowing features to be counted and measurements to be made of parameters such as area, perimeter, etc., of the features.

The term feature is used herein to describe a region within a field which is distinguishable from its surroundings by appropriate illumination. Thus a feature may be an opaque area within a translucent or transparent region or vice versa or a region of one color sorrounded by a region of another color including the case where the feature is one grey level and the surround is another grey level.

The video signal may be generated in any convenient manner but typically a television camera is employed having a target on which an image of the field is focused thereby causing the target to become partially discharged depending on the amount of light falling thereon and in which an electron beam is caused to scan the target to restore the charge thereon and the video signal is derived from the beam current variations during the scan.

It has been proposed to flash illuminate the field which may be held stationary between stepping movements, or move continuously and to scan the target with the electron beam after each flash. One or more complete scans of the target may be employed depending on the number of complete fields which are required for the analysis. However, in general a single field is all that is required and any subsequent scans are simply employed to more completely erase the charge pattern formed on the target by the image.

It is an object of the present invention to provide a mode of operation for an image analysis system which will enable the latter to be operated at a higher speed than previously for certain types of analysis.

The invention is applicable to an image analysis system adapted to examine microscopically an area which is largely black or dark grey and contains a few widely spaced small bright features. Conventionally, such an arrangement usually requires a compromise between the magnification and the time required for the analysis. If measurements are to be performed on or using the detected signal pulses it is desirable that the features are magnified as much as possible before being presented to the camera. On the other hand, high magnification means a large number of different fields of view in order to cover the area under examination. Also if the analysis is of a statistical type and it is necessary to perform measurements on a certain number of features to enable a distribution pattern to be derived from the results, the analysis will take a long time. Furthermore, where the features are widely spaced many of the fields of view will contain no features at all.

According therefore to the present invention in such a system a plurality of different, illuminated fields are presented to the scanning device between the read scans of the scanning device.

Thus in a system employing a microscope, a movable stage for presenting different images of a specimen under examination to the microscope and a television camera having the final image of the microscope focused onto its target, $n$ complete images obtained by stepping the moving stage of the microscope may be presented to the camera target and the total image formed by the $n$ separate images superimposed one on the other is then "read off" during a read scan of the camera beam. Further scans may be performed to more completely erase the charge pattern before a subsequent plurality of images are presented to the television camera.

A plurality of separate images may be obtained either by stepping the stage and illuminating each area which registers with the microscope field of view separately in turn. Alternatively and preferably the specimen under examination is moved continuously and flash illuminated in synchronism with the movement of the specimen.

Where a high speed flash rate is employed to obtain maximum advantage of the invention, the time between flashes may be insufficient to allow a read scan and subsequent erase scans to be performed thereby necessitating an interruption of the movement of the specimen and the operation of the light source. According to a preferred feature of the present invention such an interruption may be obviated if two separate scanning devices are employed and a suitable optical diverting device is employed for directing successive groups of $n$ illuminated fields alternately to the two scanning devices. In this way continuous movement of the specimen and continual operation of the flashing source may be employed and the whole time period of $n$ flashes may be employed for the read scan and subsequent erase scans.

Should the time period for the $n$ flashes be insufficient for the read and erase scans, N scanning devices may be employed (where N is greater than 2) thereby increasing the number of flash intervals during which read and erase scans can be performed on any one scanning device to $n$. (N−1).

The invention will now be described by way of example with reference to the accompanying drawings in which:

FIGS. 1–4 inclusive are FIGS. 1–4 of co-pending U.S. patent application Ser. No. 252,237, now U.S. Pat. No. 3,835,247, and FIG. 5 illustrates a circuit modification whereby the system described in co-pending application Ser. No. 252,237 can be adapted to perform the present invention.

Figure 6:
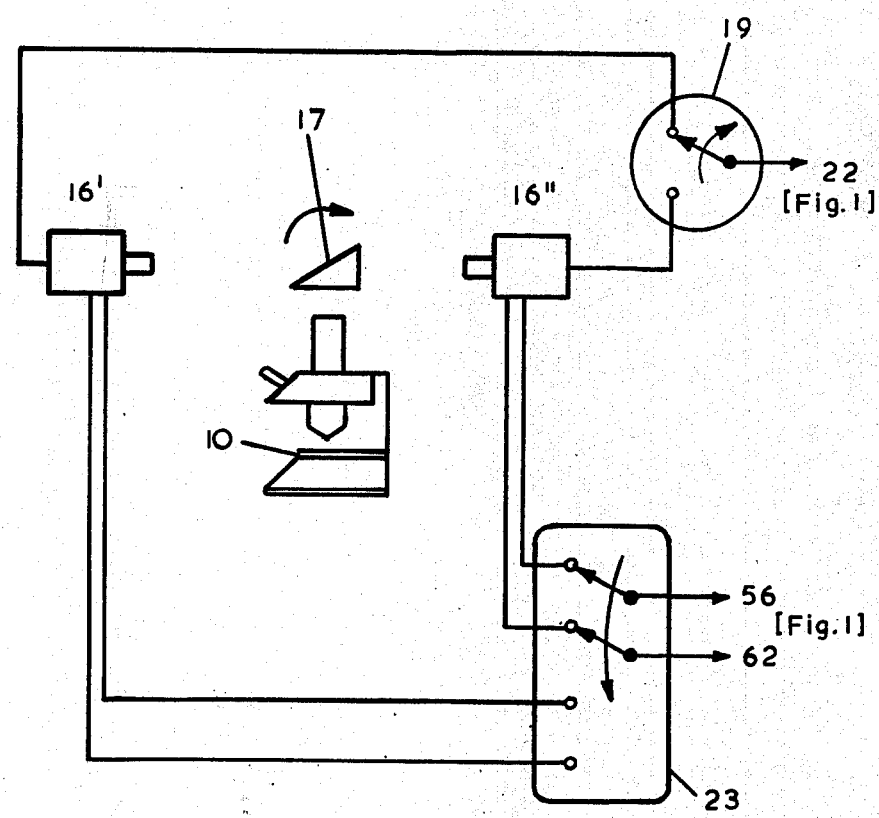

FIG. 6 illustrates a two scanner system useful in accordance with the invention.

Since FIGS. 1–4 hereof correspond to FIGS. 1–4 of co-pending U.S. patent application Ser. No. 252,237 reference is made to that application for the description of these figures of the drawings.

Figure 2:
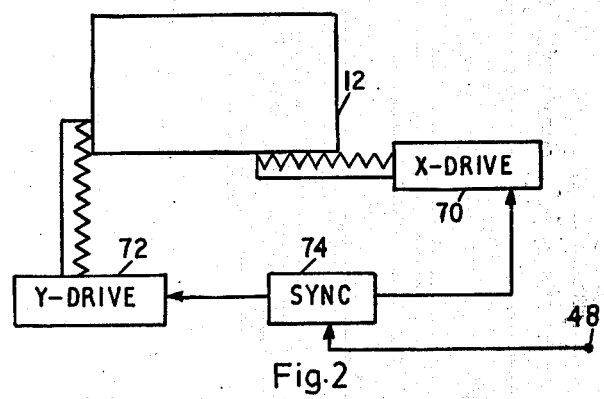
Figure 3:
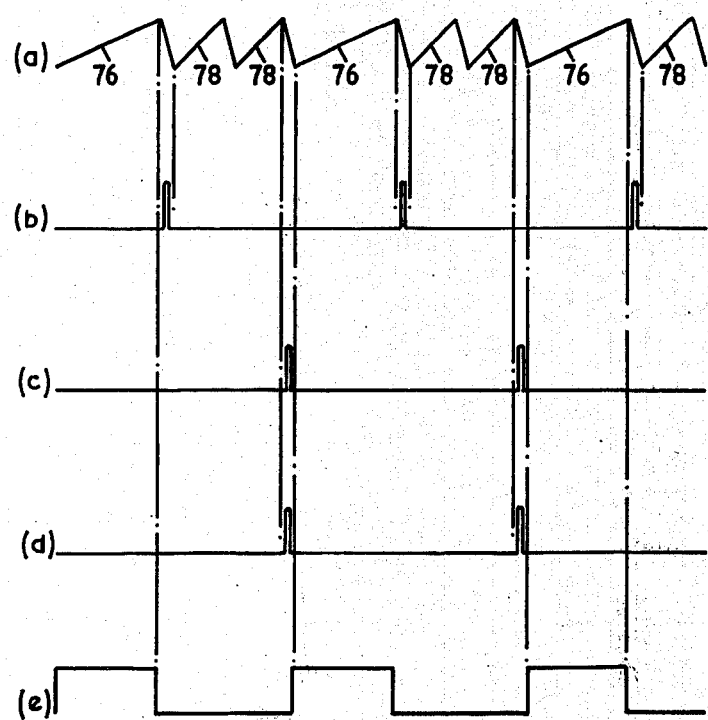
Figure 4:
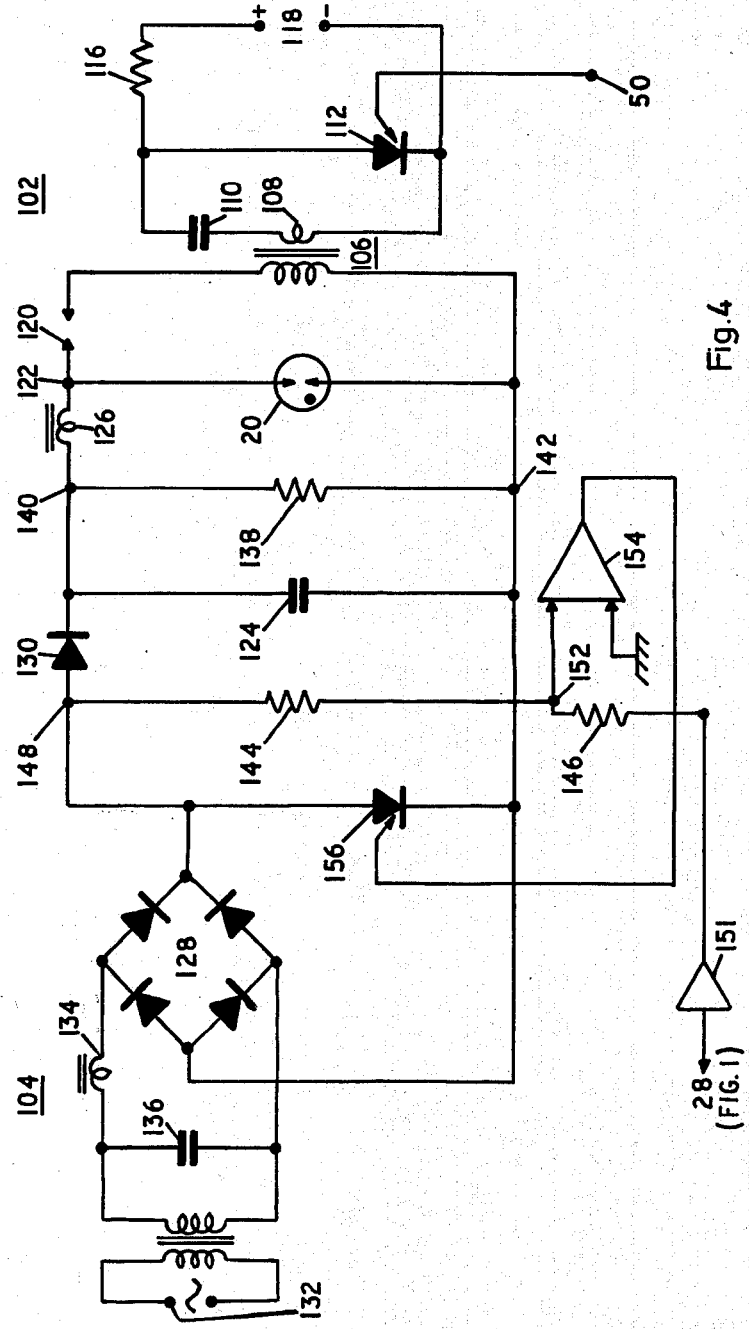
Figure 5:
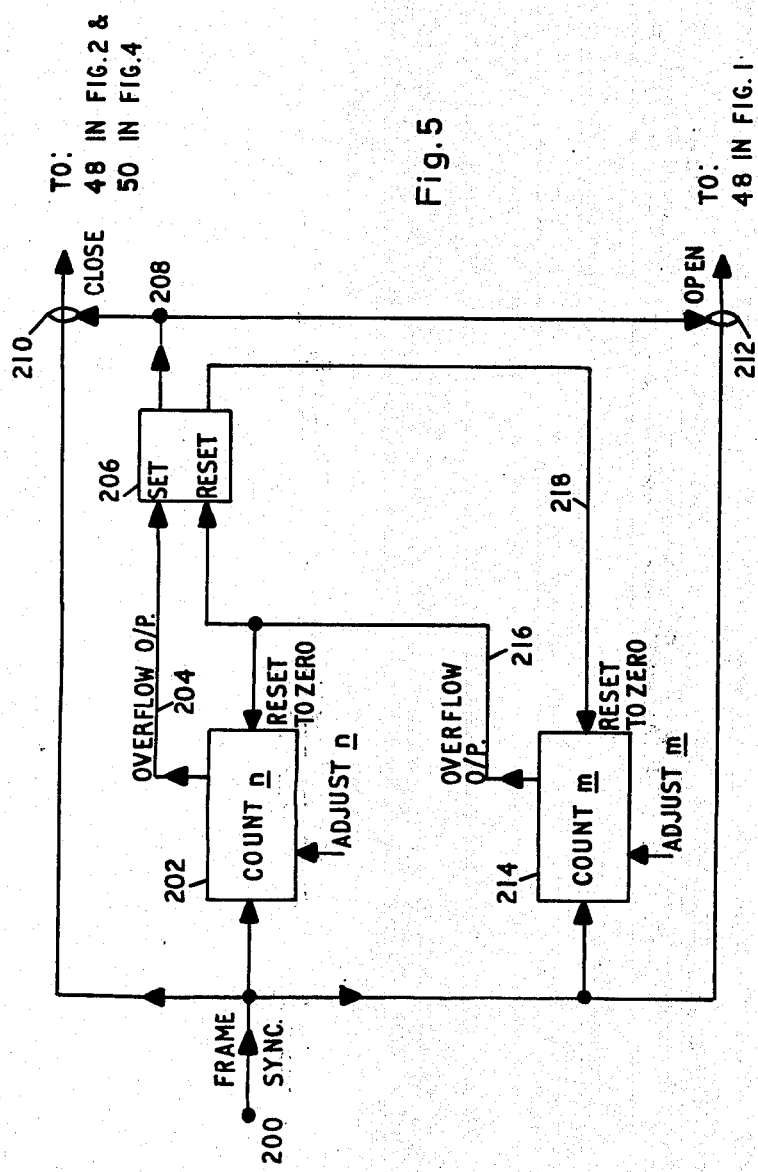

The modification to the circuit of FIGS. 1, 2 and 4 of the drawings of co-pending application Ser. No. 252,237 to perform the present invention is illustrated in FIG. 5. In this figure the frame synchronizing pulses are applied to junction 200 and are counted by a first counter 202 which produces an overflow signal along line 204 when the counter reaches its capacity. Preferably an adjustable capacity counter is employed so that the value of $n$ can be adjusted. The counter includes a RESET input which when an appropriate electrical signal is applied thereto resets the counter to zero.

The overflow signal on line 204 constitutes a SET signal for a bistable device 206 the SET output of which is applied to junction 208. The signal at 208 serves as a close signal for a gate 210 and an open signal for a gate 212. Gate 210 controls the passage of the frame synchronizing pulses to junction 48 of FIG. 2 of co-pending application Ser. No. 252,237 and to terminal 50 in FIG. 4 of co-pending application Ser. No. 252,237.

Gate 212 likewise controls the passage of frame synchronizing pulses to junction 48 of FIG. 1 of co-pending application Ser. No. 252,237.

It will be noted that when gate 210 is closed gate 212 is open and vice versa.

The time during which gate 212 is open is determined by a second counter 214 to which frame synchronizing pulses from junction 200 are also applied. This counter is similar to counter 202 and is also of adjustable count capacity. When the counter reaches its capacity, an overflow signal appears along line 216 and this is applied as a reset signal to the bistable device 206 and also as the reset signal to counter 202. The reset output of bistable device 206 is applied along line 218 to the reset terminal of counter 214 to reset the counter to zero.

It will be noted that the reset condition of bistable 206 inhibits counter 214 and the overflow signal along line 216 (which would otherwise inhibit counter 202) is removed as soon as bistable device 206 has reset.

The action of the circuit is to allow the first $n$ frame synchronizing pulses which appear at junction 200 to pass through gate 210 causing the stage to step an appropriate number of times via x and y drives 70 and 72 (see FIG. 2) and to cause the lamp 20 to flash once for each of the fields presented to the scanner. At the end of these $n$ frame scans gate 210 is closed and gate 212 is opened allowing the next $n$ frame synchronizing pulses to pass to junction 48 of FIG. 1. It is to be noted that when incorporating the circuit of FIG. 5, gate 40 (which comprises the Thyristor of FIG. 4) is no longer controlled by signals at junction 50 in FIG. 1. In consequence connection 220 must be broken. Control signals for gate 40 (i.e. Thyristor 112) are obtained as previously described via gate 210 of FIG. 5.

In one example the capacity of counter 202 is set to 5 and that of counter 214 is set to 2. In this way five successive fields will be presented to the scanner and the five images combined by the accumulating action of the scanner target after which a read scan will be performed followed by two erase scans at twice normal scan rate. At the end of this sequence the stage will be stepped again and the lamp flashed to present a further five fields to the scanner and the read and erase scans will follow as previously described.

Where the frame scan time and erase interval will allow, continuous movement of the stage is possible at least in the x direction thereby reducing the settlement time required. Where the time required for the erase scans will not allow continuous movement, two scanners 16' and 16" may be employed as shown in FIG. 6 and an optical diverting device 17 employed to divert the image of the field from one scanner to the other. Each scanner 16', 16" comprises a television camera. Synchronously operated gating means 19 is provided to switch the outputs from the two separate scanners to junction 22. In a similar way gating means 23 is provided for supplying the frame scan signals from junctions 56 and 62 to the appropriate one of the scanners.

A further modification is necessary in FIG. 1. This involves the disconnection of the link 220 and the connection of the control terminal for gate 40 to junction 48 of FIG. 1. The lamp 20 is therefore caused to flash at the beginning of each frame scan.

In operation the first $n$ frame scan synchronizing pulses appearing at junction 48 will cause $n$ fields to be presented and flash illuminated to the first camera which during this interval is disconnected from junction 22 and is also disconnected from the frame scan deflection signal generator. At the end of this interval, the connections are reversed so that the first scanner is now connected to junction 22 and to the frame scan generator (junctions 56 and 62 in FIG. 1) whereupon a read scan is performed followed by a plurality of erase scans determined by the capacity of divider 46 and counter 64. The count capacities of these two devices are adjusted so that after the read scan, the remainder of the interval is fully occupied with erase scans. At the end of this second interval, the connections are reversed once again and the next $n$ images are supplied to the first scanner and the process repeated.

During the read and erase scans performed on the first scanner, the next $n$ flash illuminated fields are presented to the second scanner and at the end of these $n$ fields, when the connections are reversed, the accumulated charge pattern on the second scanner is read off during the read scan and the target is cleared by the succeeding erase scans as previously described.

Where two scanners and gating circuits as described are employed, there is no need for the modification of FIG. 5 which is simply provided to modify the single scanner circuit of FIG. 1 to perform the invention.

The invention relies for its success on the assumption that during $n$ successive fields no two of the small widely separated bright features will occupy the same position in the field of view. Accordingly an appropriate magnification and field of view must be employed having regard to the number and dispersion of the small bright features to ensure that there is a high probability that no such overlap of feature position will occur between successive fields.

However, a value for $n$ lower than that obtainable from spacing/magnification/field of view considerations alone will probably have to be adopted due to the build-up of electrical noise and background level in the charge pattern developed by successive fields presented to the scanning device. Thus $n$ will probably be limited to a value obtained by dividing the percentage video signal amplitude excursion (including noise) due to a typical feature by that due to the background and noise. Thus if a typical feature produces a 50 percent modulation including noise and background and noise produces a 10 percent modulation of the video signal amplitude, then $n$ is limited to 5.

What is claimed as new and desired to be secured by Letters Patent of the United States is:

1. Apparatus for analyzing microscopically a specimen containing a few widely spaced small features comprising, in combination, a microscope, a moveable stage for presenting different regions of a specimen mounted thereon to the microscope and a television camera having the final image of the microscope focused onto its target, means for stepping the stage of the microscope to present different fields of view thereto, means for flash illuminating each different field of view, circuit means for generating $n$ control signals for the means for stepping the stage and the means for flash illuminating the field of view, additional circuit means for inhibiting at least the frame scan deflection signals normally supplied to the television camera during the $n$ different fields of view, further circuit means for inhibiting the video signal output from the television camera during said $n$ different fields and still further circuit means for generating deflection signals to perform a read scan of said television camera and a succession of erase scans after said $n$ fields have been presented thereto.

2. Apparatus as claimed in claim 1 in which the stage is moved continuously and the flash illumination is synchronized with the movement of the specimen so as to reduce the time required to present $n$ successive different fields of view to the microscope.

3. Apparatus as claimed in claim 1 further comprising a second scanning device, an optical diverting device for directing each successive group of $n$ illuminated fields alternately to the two scanners, switch means for inhibiting at least the frame scan deflection signals to one scanner and the video signal output therefrom whilst supplying frame scan deflection signals to the other scanner and releasing the video signal obtained therefrom and additional circuit means adapted to reverse the connections to the scanners at the end of each $n$ succeeding fields of view.

4. Apparatus as claimed in claim 2 further comprising a second scanning device, an optical diverting device for directing each successive group of $n$ illuminated fields alternately to the two scanners, switch means for inhibiting at least the frame scan deflection signals to one scanner and the video signal output therefrom whilst supplying frame scan deflection signals to the other scanner and releasing the video signal obtained therefrom and additional circuit means adapted to reverse the connections to the scanners at the end of each $n$ succeeding fields of view.

* * * * *